United States Patent
Al Alawi et al.

(10) Patent No.: US 9,616,044 B2
(45) Date of Patent: Apr. 11, 2017

(54) LONG ACTING COMPOSITIONS

(71) Applicant: BAYER NEW ZEALAND LTD, Hamilton (NZ)

(72) Inventors: Fadil Al Alawi, Hamilton (NZ); Karthigeyan Nanjan, Hamilton (NZ)

( * ) Notice: Subject to any disclaimer, the term of this patent is extended or adjusted under 35 U.S.C. 154(b) by 0 days.

(21) Appl. No.: 14/384,308

(22) PCT Filed: Mar. 13, 2013

(86) PCT No.: PCT/NZ2013/000036
§ 371 (c)(1),
(2) Date: Sep. 10, 2014

(87) PCT Pub. No.: WO2013/137748
PCT Pub. Date: Sep. 19, 2013

(65) Prior Publication Data
US 2015/0038565 A1    Feb. 5, 2015

(30) Foreign Application Priority Data

Mar. 13, 2012   (NZ) ........................................ 598757

(51) Int. Cl.
| | | |
|---|---|---|
| *A61K 31/365* | (2006.01) | |
| *A61K 47/22* | (2006.01) | |
| *A61K 9/08* | (2006.01) | |
| *A61K 47/44* | (2017.01) | |
| *A61K 31/7048* | (2006.01) | |
| *A61K 9/00* | (2006.01) | |

(52) U.S. Cl.
CPC .......... *A61K 31/365* (2013.01); *A61K 9/0019* (2013.01); *A61K 9/08* (2013.01); *A61K 31/7048* (2013.01); *A61K 47/22* (2013.01); *A61K 47/44* (2013.01)

(58) Field of Classification Search
CPC .................................................... A61K 31/365
See application file for complete search history.

(56) References Cited

U.S. PATENT DOCUMENTS

| 6,159,932 A | 12/2000 | Mencke et al. |
|---|---|---|
| 2002/0160967 A1 | 10/2002 | Grosse-Bley et al. |
| 2003/0166688 A1 * | 9/2003 | Soll et al. .................... 514/341 |
| 2006/0257440 A1 | 11/2006 | Asai et al. |

FOREIGN PATENT DOCUMENTS

| AU | 2002100152 A4 * | 4/2002 |
|---|---|---|
| AU | 2002100152 B4 | 4/2002 |
| AU | 2005100403 B4 | 6/2005 |
| BR | PI1001224 A2 | 3/2011 |
| CN | 1383821 A | 12/2002 |
| CN | 1490009 A * | 4/2004 |
| CN | 1583174 A | 2/2005 |
| CN | 1293921 C | 1/2007 |
| EP | 0427582 A2 | 5/1991 |
| EP | 1136081 B1 | 1/2005 |
| EP | 2345413 A2 | 7/2011 |
| NZ | 332224 A | 6/2000 |
| NZ | 535644 A | 5/2007 |
| WO | 9711709 A1 | 4/1997 |
| WO | 0160380 A1 | 8/2001 |
| WO | 2005037294 A1 | 4/2005 |
| WO | 2010008891 A2 | 1/2010 |
| WO | 2010116267 A1 | 10/2010 |
| WO | WO 2012089623 A1 * | 7/2012 |

OTHER PUBLICATIONS

Merck Veterinary Manual, 9th Edition, Extracts, p. 2115-2117, 2122-2124, 2161-2165, (c) 2015.
Material Safety Data Sheet for Genesis Injection Abamectin Antiparasitic for Cattle & Sheep from Ancare, revision Feb. 2008.
Product Registration for Ectoparasiticide, downloaded from the website of New Zealand Ministry for Primary Industries, May 30, 2015.
Material Safety Data Sheet for Dectomax Injectable Endectocide from Pfizer, revision May 2009.
Material Safety Data Sheet for Endoectocide for ectoparasite and endoparasite control on cats Veterinary medicine, from Bayer HealthCare Animal Health, Mar. 25, 2009.
IVS Annual 2006 Product Listings for Genesis Injection and Ivomec Injection for Cattle, Sheep and Pigs, CMPMedica, 2006, 21: Extract 339, 345-346.
The Veterinary Formulary, Pharmaceutical Press, Ed. Yolande Bishop, Sixth Edition, Extract, 2005: 201-209.
McKellar and Benchaoui, "Avermectins and Milbemycins," J. Vet. Pharmacol. Therap. 1996, 19: 331-351.
Spiegel and Noseworthy, "Use of Nonaqueous Solvents in Parenteral Products," Journal of Pharmaceutical Sciences, 1963, 52(10): 917-927.
Handbook of Pharmaceutical Excipients, 6th Edition, Editors Rowe, Sheskey and Quinn, Pharmaceutical Press, 2009, Extracts: 75-76, 126-127, 682-685.
Sanghvi et al, "Solubility Improvement of Drugs using N-Methyl Pyrrolidone," AAPS, PharmSciTech 2008, 9(2): 366-376.
Jouyban et al, "Review of Pharmaceutical Applications of N-Methyl-2-Pyrrolidone," J Pharm Pharmaceut Sci, 2010, 13 (4): 524-535.
ACVM Registration for Dectomax, (c) 2015.
ACVM Product Label for Dectomax, (c) 2015.
ACVM Registration for Genesis Injection, (c) 2015.
ACVM Registration for Cydectin Injection, (c) 2015.
ACVM Registration for Ivomec Injection for Cattle, Sheep and Pigs, (c) 2015.
ACVM Registration for Noromectin Injection for Cattle, Sheep and Pigs, (c) 2015.
ACVM Registration for Ivomec Pour-On for Cattle and Deer, (c) 2015.
ACVM Registration for Noromectin Pour-On for Cattle and Deer, (c) 2015.

* cited by examiner

*Primary Examiner* — Noble Jarrell
*Assistant Examiner* — John S Kenyon

(57) ABSTRACT

The present invention relates to a long-acting composition for the treatment of an animal in need thereof wherein the composition includes a therapeutically effective amount of a bioactive agent, characterized in that the composition includes a non-aqueous carrier and a solvent system comprising castor oil and at least one cyclic amide.

18 Claims, 3 Drawing Sheets

LONG ACTING COMPOSITIONS

TECHNICAL FIELD

Figure 1:
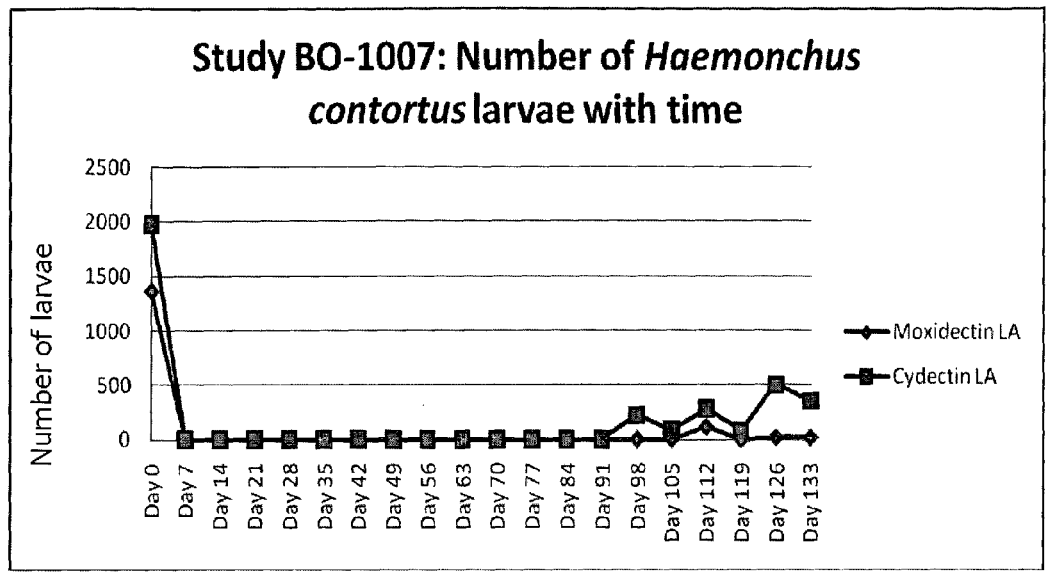

The present invention relates to a long acting composition including a bioactive, and particularly, but not limited to, compositions for the treatment or prevention of parasitic infections in or on an animal.

BACKGROUND ART

In the medical and veterinary fields, there is need and long felt want to provide improved long acting compositions. A significant advantage of utilising long acting compositions is the ability to administer the composition on a less frequent basis. This equates to less stress, time and hardship to the patient or animal, as well as the caregiver. Less consumables and storage of the composition is also required, also giving significant advantages.

Whilst there are many known bio-active agents already in use, it can often be difficult to provide these in compositions with good pharmacokinetic properties, including in this case, long acting delivery profiles.

Problems often persist with poor stability or solubility of the actives, uncontrolled or unwanted release profiles, poor knockdown affects or unwanted side effects following administration.

For example, in the field of veterinary medicine, anthelmintics are used to control or treat internal and external parasites. There is a wide variety of different anthelmintics and derivatives to utilise when treating such parasites. However, many anthelmintics, such as macrocyclic lactones, are poorly soluble in conventional solvents. They are particularly difficult to administer in an injectable format, which is typically used for long acting protection against ecto- and endoparasites.

Macrocyclic lactone compounds such as avermectins, ivermectin, doramectin, mibemycin and moxidectin can easily break down in water-based compositions.

To try to counter this issue, formulation chemists have included such actives together with excipients such as glycol solvents, glycerol formal and/or surfactants.

However, an additional significant problem encountered with many anthelmintic compositions, many of which attempt to provide a long acting persistence, is that the macrocyclic lactone is released too rapidly in the animal. This leads to a shorter duration of protection from the active, disadvantageously requiring re-administration on a more regular basis.

It can also be very dangerous to animals to be exposed to high levels of the bioactive agent (e.g. a macrocyclic lactone), especially younger animals such as calves under the age of 10 weeks. A further problem is therefore trying to avoid an uncontrolled release profile of the active to avoid toxic results.

Furthermore, it is often be beneficial to provide a controlled "burst" of an active agent to provide an initial "knockdown effect" to help rid the body of parasites. This controlled burst can then be followed with a long acting slow release of the anthelmintic to help ensure the parasites are completely removed, or provide long term protection.

A controlled profile release such as this can be difficult to achieve, especially in a single long acting composition. This is especially true for precarious actives such as anthelmintics. Even if such a release is achieved, it often comes at the expense of complicated combination of excipients, increased labour in manufacture, equipment or other resources in preparing the composition.

Injectable compositions can be especially troublesome to formulate as long acting compositions. For instance, many of the excipients used such as polymers, glycols, alcohol based solvents and so forth can lead to unwanted characteristics such as high viscosity in the composition which can make it difficult to administer through a needle. Similarly, some of the excipients used in long acting injectables can lead to an increased site reaction on injection. Also, some compositions can have poor storage characteristics. Furthermore, despite attempting to provide a long acting release of active and therefore persistency of protection, many fall short of this goal.

WO 97/11709 (Harvey) discloses an anthelmintic lactone composition including a vegetable oil and a co-solvent chosen from an alcohol having four or more carbon atoms, such as benzyl alcohol.

U.S. Pat. No. 6,552,002 (Steber) discloses sustained-release compositions including a macrocyclic lactone compound at a high concentration (between 5-30% w/w), together with a surfactant (described as sorbitan esters), a solvent and co-solvent.

Steber discusses that by increasing the active concentration above what is normally used, a sustained release of the active is possible. However, higher loading of actives can be dangerous due to toxicity problems as previously discussed.

Furthermore, the higher concentration of active needed to provide the sustained release profile in Steber requires a complicated combination of excipients. Despite these requirements, it is likely the high loading of active could inherently lead to stress on the composition, leading to a diminished shelf life. Other downfalls include likely higher costs in preparation and/or a greater site reaction on delivery.

U.S. Pat. No. 6,174,540 (Williams) discloses long acting injectable formulations including a therapeutic agent (e.g. insecticides, parasiticides, NSAIDs, etc) together with hydrogenated castor oil, a hydrophobic carrier (triacetin, benzyl benzoate, or ethyl oleate), and one of acylated monoglycerides, propyl dicaprylates/dicaprate, or caprylic/capric acid triglycerides). Williams found that the combination of excipients identified, as expected, had the ability to provide a long acting release profile to a range of bioactives.

NZ 332224 (Grosse-Bley) also discloses injectable formulations including avermectins and mibemycins which include castor oil together with an additional co-solvent selected from fatty acid esters of mono- or polyhydric alcohols, aliphatic or aromatic alcohols, or cyclic carbonates.

WO 2007/024719 (Soil) discloses long acting injectable formulations for treating ectoparasites and endoparasites, wherein the formulation includes the bioactive agent, a subcutaneously volatile solvent, a biologically acceptable polymer, together with additional optional excipients. The use of polymers especially was discussed as allowing the release profile to extend up to 42 days.

EP 393890 (Wicks) discloses the use of a combination of ethyl oleate (a fatty acid ester) and sesame oil as a solvent for avermectin compounds. These formulations were found to be well tolerated when administered as an injection. However they lack storage stability, with a precipitate forming after a few days when stored at 4° C.

WO 2010116267 (Costa) discloses high-dose injectable formulations of doramectin at 3.5% in a carrier of cottonseed oil and benzyl benzoate. A comparative example is a formulation from NZ 332224 (Grosse-Bley), containing 3% doramectin in a carrier of 40% v/v castor oil and 60% v/v ethyl oleate. Costa provides a comparison of the efficacy in treating screwworm (the larvae of the myiasis-causing fly *Cochliomyia hominivorax*), between the disclosed cottonseed oil/benzyl benzoate composition and the comparative castor oil composition in Grosse-Bley. The results showed that the release of active from the castor oil formulation is either delayed or relatively slow, so that an efficacious systemic concentration is reached noticeably later than the cottonseed/benzyl benzoate formulation. It was suggested that the high affinity of castor oil for avermectins such as doramectin, unfavourably slows the release of the drug from the carrier.

A currently available commercial product Cydectin® Long Acting Injection for Sheep is marketed as a long-acting formulation containing moxidectin. This product is indicated to prevent reinfection with *Haemonchus contortus* for 91 days, *Ostergia circumcincta* for 112 days and *Trichostrongylus colubriformis* for 42 days following a single dose. Preliminary studies performed by the current inventors assessed larvae counts from hatched eggs from faecal samples. This study found that Cydectin® Long Acting provided a reduced egg count for up to about 100 days.

Furthermore, Cydectin can lead to site reaction (e.g. swelling and inflammation) at the injection site in animals following administration.

There is a long felt need to provide stable, long acting formulations that can provide protection against parasites for longer duration than currently available compositions like Cydectin®.

Even more so, there is a need to provide a formulation that provides a treatment that allows a fast yet controlled "bleed" to provide a good initial knockdown effect to quickly control the condition in the animal, yet then still provide a longer acting protection to the animal.

Despite the attempts in the industry to formulate long acting compositions, the problems outlined above continue to persist.

It is an object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

Throughout this specification, the word "comprise", or variations thereof such as "comprises" or "comprising", will be understood to imply the inclusion of a stated element, integer or step, or group of elements integers or steps, but not the exclusion of any other element, integer or step, or group of elements, integers or steps.

Further aspects and advantages of the present invention will become apparent from the ensuing description which is given by way of example only.

DISCLOSURE OF INVENTION

According to one aspect of the present invention there is provided a long acting composition for the treatment of an animal in need thereof wherein the composition includes a bioactive agent, characterised in that the composition includes a non-aqueous carrier and a solvent system comprising castor oil and at least one cyclic amide.

Throughout this specification the term "long acting" should be taken as meaning being effective after an initial dosage and maintaining its effects over an extended period of time.

Preferably, the term long acting nature of the composition provides an acceptable and persistent efficacy for more than 40 days after an initial dosage.

Advantages of the Present Invention

The inventors surprisingly found that a composition of the present invention gave both rapid-knockdown and excellent long acting characteristics of the composition when delivered to an animal.

Without wishing to be bound by theory, the inventors believe the advantageous properties of both rapid knockdown, and good long-term persistency of the present invention may be provided the combination of castor oil with the at least one cyclic amide solvent.

The inventors believe that the cyclic amide solvent allows an initial release of bioactive agent in the short term, leaving behind the castor oil to provide a longer release of the bioactive agent over an extended period of time. In other words, the castor oil and cyclic amide solvent are thought to provide a biphasic release of the active agent from the injection site over time, which act synergistically together to provide a substantiated release profile of the active agent.

This biphasic release is expected to be seen when used with substantially any active agent, despite the present invention most preferably using an anthelmintic such as moxidectin.

The inventors foresee the composition may also be used to provide a controlled short term "burst" of bioactive release after delivery to provide an initial knockdown effect, followed by a longer term delivery of the bioactive agent. This may be very useful to treat more acute conditions where the bioactive agent is needed at higher levels in the short term to quickly stabilise or treat the animal, but at lower levels over the longer term (e.g. once the condition's severity has lessened). Without this advantageous release profile, a caregiver may otherwise need to deliver two treatments administered simultaneously or consecutively to achieve the same result.

In summary, some advantages of the present invention may include:
- allowance of one dosage opposed to repeated dosages to avoids extra handling stress to the animal;
- a sustained release profile of the bioactive, over both the short term period and long term period after delivery;
- avoidance of toxicity problems which can otherwise be caused by uncontrolled release of the active;
- improved persistency and knockdown effect compared to commercially available long acting compositions such as Cydectin® (see below)
- avoidance of high loading of active agent to achieve longer persistency as taught in Steber et al.) and thereby reducing potential side effect, or instability of the composition etc;
- long term storage stability
- efficiency in the manufacturing process
- little to no site reaction on delivery. Lower dose trials showed no site reaction. Higher dose trials (discussed below) showed minimal site reaction similar to Cydectin®. This was unexpected as the inventive composition appears to provide a slower release from the injection site, therefore a higher site reaction than Cydectin® was expected.

Comparison to Cydectin:

When an exemplary composition of the present invention was compared to Cydectin® (a long acting moxidectin injection) preliminary results showed significantly higher residues in subcutaneous fat after 90 days compared to the withhold period of Cydectin®. This strongly supports the greater persistency provided by the present composition. The studies were set up to ensure that the same active ingredient (moxidection) and concentration were used in the test composition as present in Cydectin®.

These studies suggest moxidectin may be being absorbed into the fat tissues more effectively than seen with Cydectin®. It is possible that the rate of uptake of moxidectin into the fat tissue has a maximum limit irrespective of the concentration in the blood. Therefore, a potentially slower release from the injection site offered by the present invention may actually allow greater amounts of the active to be absorbed into the fat.

Once in the fat tissue, it is thought moxidectin is then slowly released into other tissues.

In Cydectin®, it is possible that the active agent that is released quicker is being cleared from the bloodstream and/or injection site by other means such as the liver, thereby preventing efficient transfer to the fat tissue.

It is also possible that a higher dosage of active agent may help to achieve the illustrated persistency, which might assisted by the slow release from the injection site. However, given that Cydectin® included this same dosage of 2% w/w as the tested formulation, it is thought a high level of moxidectin cannot be the sole reason for the improved results as seen.

PREFERRED EMBODIMENTS

Preferably, the composition is configured for parenteral injection.

A significant advantage of the present composition is that the excipients used allow a good consistency for easy injection. Similar compositions currently available, such as Cydectin® can be quite viscous, which can be difficult for injection, and potentially painful or harmful to the animal. For example, Cydectin® requires a special injector to be used due to its viscosity requirements. In preliminary studies, the trial products of the present invention appeared easier to administer than Cydectin®.

However, the ability of the composition to provide a beneficial long acting release profile may easily be adapted for other routes of administration, using known excipients commonly used in the industry. Such modes of delivery may include topical (such as composition adapted for a spot-on or spray-on), oral (such as composition adapted for tablets or drenches), or internal (such as a composition adapted as a bolus).

Preferably, the bioactive agent is an anthelmintic compound.

The anthelmintic may be present in the composition at a concentration between 0.005 to 30% w/v.

Preferably, the anthelmintic is present in the composition at a concentration between 0.005 to 5% w/v.

A significant advantage of the present invention is that a desired release profile may be achieved using normal and safe amounts of anthelmintic agent. This is unlike U.S. Pat. No. 6,552,002 (Steber) which discusses the need to increase the active concentration to 5-30% in order to achieve a suitable release profile, potentially putting the animal at risk of toxic doses of active agent.

Clearly, if an alternative bioactive agent is used, the amount of bioactive agent may be adjusted accordingly to suit clinical and pharmacokinetic requirements.

However, the inventors acknowledge that the bioactive agent may alternatively be any bioactive, such as an insecticide, parasiticide, growth enhancer, anti-infective or NSAID without departing from the scope of the invention. It would be reasonably expected that the inventive combination of an oil together with a cyclic amide solvent may be used with any bioactive agent which requires a long acting release profile as outlined above. This is supported by the disclosure in U.S. Pat. No. 6,174,540 (Williams) which identified that the combination of excipients could be utilised with a range of bio-actives yet still provide the desired outcome.

The inventors particularly consider the present invention would work well with substantially any macrocyclic lactone compounds such as avermectins and milbemycins.

Preferably, the anthelmintic is selected from the group consisting of avermectin, moxidectin, milbemycin, ivermectin, abamectin, doramectin, eprinomectin and selamectin.

Preferably, the anthelmintic is moxidectin.

Moxidectin is the most preferred active agent as it has a known persistency at therapeutic levels for an extended period of time, as exemplified by Cydectin®. Moxidection also has a high level of efficacy, a broad spectrum of activity and is relatively safe to use.

Regardless, it should be appreciated that the present invention extends to use of other types of actives and compositions including same without departing from the scope thereof.

Castor oil was found to be useful as part of a solvent system for the active agent, and particularly beneficial in providing a sustained release of the active agent.

The castor oil may be present in the composition at a concentration between 1-70% w/v.

Preferably, the castor oil is present in the composition at between 1-20% w/v.

More preferably, the castor oil is present in the composition at between 1-15% w/v.

The inventors found that a concentration of approximately 7% w/v castor worked particularly effectively. This amount of castor oil tended to result in the active being released synergistically at an optimal rate from the injection site.

The composition includes a non-aqueous carrier.

Preferably the non-aqueous carrier is chosen to provide appropriate physical properties to the composition, such as suitable viscosity and tolerability when administered.

Preferably the non-aqueous carrier is a hydrophobic vehicle such as an oil.

Preferably the oil is of a vegetable, animal or synthetic origin.

More preferably, the carrier is selected from the group consisting of canola oil, corn oil, cottonseed oil, olive oil, peanut oil, sesame oil, soybean oil, safflower oil, coconut oil, sunflower oil, palm oil, monoglycerides, diglycerides and triglycerides, medium chain succinic acid triglyceride, caprylic/capric triglyceride, caprylic/capric/linoleic triglyceride, caprylic/capric/succinic triglyceride.

Most preferably, the carrier is soyabean oil.

Preferably the active is insoluble or relatively insoluble in the non-aqueous carrier without the presence of the solvent system.

The inventors found that the combination of castor oil from the solvent system and soyabean oil as the carrier provided particularly useful sustained release characteristics. This is thought to be due to the soyabean oil as being a relatively inert carrier that acts as a vehicle for administering the active solubilised by the solvent system.

The cyclic amide solvent may be present in the composition at a concentration between 1-50% w/v.

Preferably, the cyclic amide solvent is present in the composition at a concentration of approximately 15% w/v.

Figure 2:
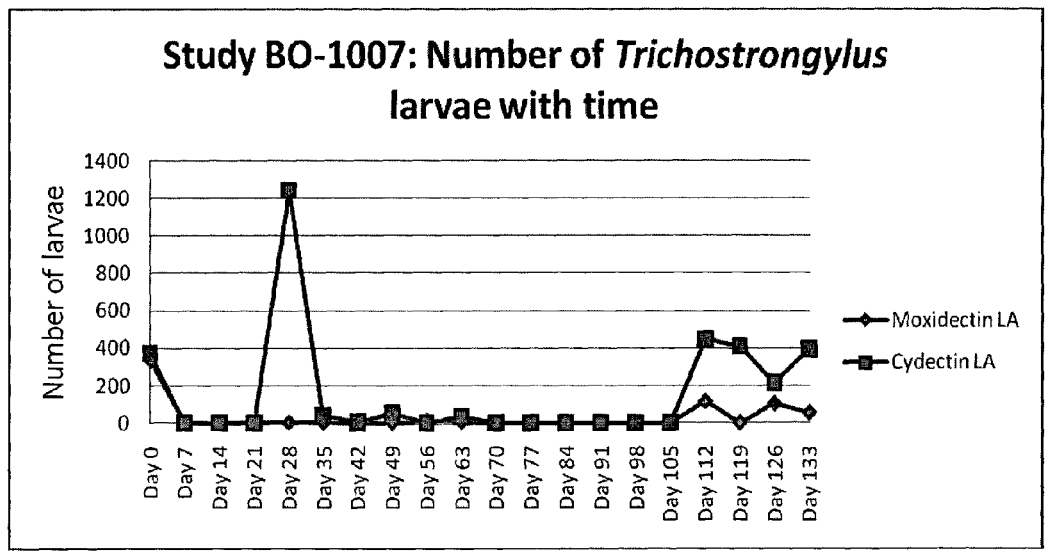
Figure 3:
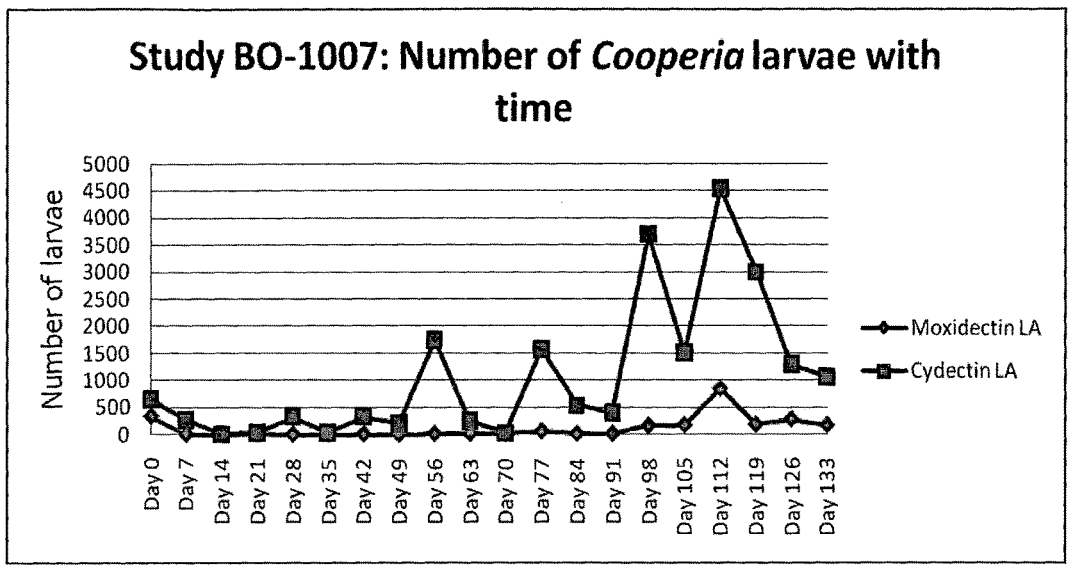
Figure 4:
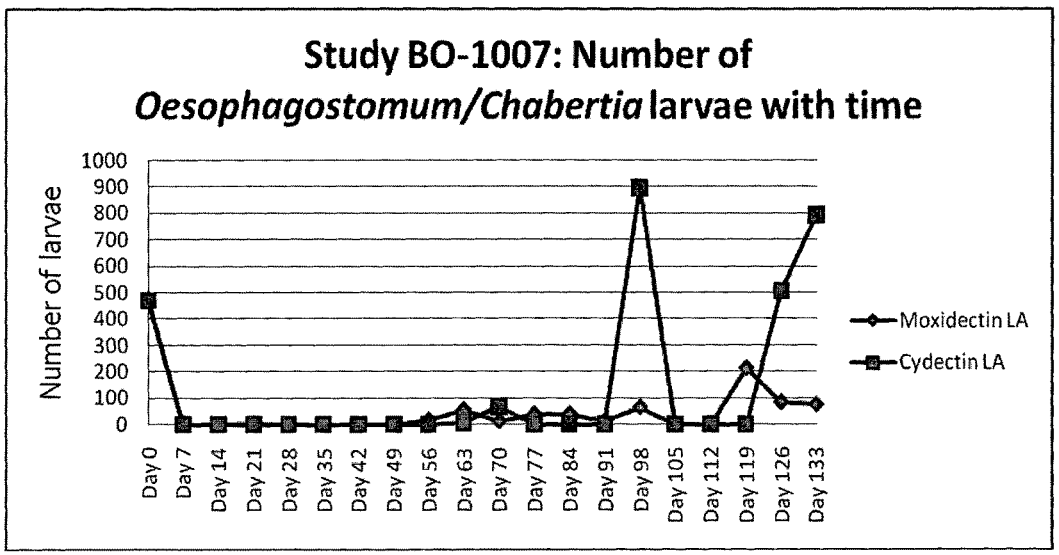
Figure 5:
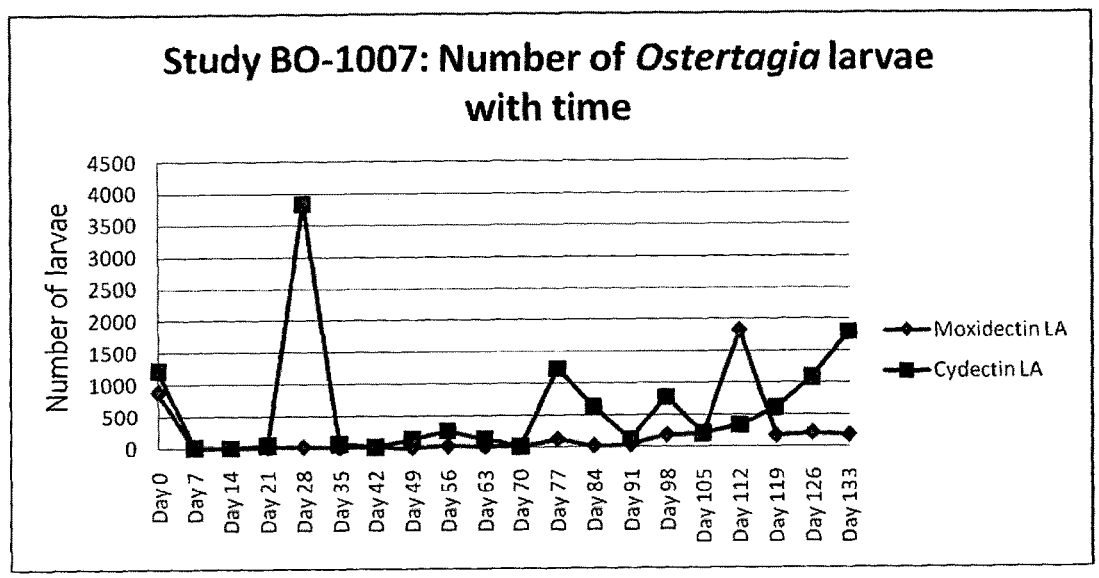

The inventors identified that the use of the cyclic amide solvent in a long acting composition allows an initial "bleed" of the bioactive before the long acting release of the composition is governed by the remaining oil. A significant disadvantage identified in the prior art with using castor oil as a solvent, particularly with avermectins and milbemycins, is that if the affinity between the active and castor oil is too high, the release of the active can be too slow. This may delay the effect of the active, prevent the active from being entirely effective, and/or increase the likelihood of resistance developing. The use of a cyclic amide in combination with castor oil as the solvent system, surprisingly overcomes this problem.

Without wishing to be bound by theory, the inventors believe that the cyclic amide solvent may be able to form a complex with the active, which rapidly releases some of the active from the administered composition into the animal. The remainder of the active is then able to more slowly release from the composition, enabling the long-acting effect.

Additionally, the combination of the cyclic amide solvent and castor oil solvent may help to lower the requirement of the castor oil compared to the prior art. This may advantageously provide a greater ability to control the release rate/long acting effect.

Furthermore, the inventors identified that manipulation of the concentration of the cyclic amide solvent may allow careful control of the rate of this initial "bleed". This may provide the ability to carefully alter the initial release profile of the composition, depending on the condition to be treated or the severity of the condition in the animal. This may be an advantage as long-acting formulations can be notoriously difficult to control, often with uncontrolled initial release of the active.

Preferably, the cyclic amide solvent is a pyrrolidone.

More preferably, the pyrrolidone is selected from the group consisting of 1-methyl-2-pyrrolidinone (NMP), 2-pyrrolidone and combinations thereof.

Most preferably, the cyclic amide solvent is NMP. An advantage of NMP is that it is commonly used in the pharmaceutical industry, it is well accepted and is relatively inexpensive.

A particularly preferred composition includes moxidectin as the bioactive agent, together with a combination of castor oil and NMP.

The composition may include an antioxidant. Substantially any antioxidant may be used. However, the inventors consider particularly useful antioxidants may be butylated hydroxyanisole (BHA), butylated hydroxytoluene (BHT) or a combination of both.

In the literature, antioxidants have been used to stabilise a macrocyclic lactone compound in a composition. However, if a macrocyclic lactone compound is combined together with another active, the antioxidant is often not sufficient to stabilise the composition. The composition of the present invention may allow multiple actives to be combined together (such as a macrocyclic lactone and levamisole), yet also allow the antioxidant to be present to perform its normal antioxidant function and/or help stabilise the formulation.

Typically, the antioxidant may be present in the formulation between 0.005 to 10% w/v.

Preferably, the antioxidant is BHT and is present in the composition at a concentration of approximately 0.05% w/v.

Other carriers or excipients may include any of the following: acetins (mono, di and triacetin), ethyl oleate and benzyl benzoate.

Method of Treatment

A method of treating an animal in need thereof with a composition as discussed above, including the step of delivering the composition to the animal to provide long acting protection against or treatment for a condition or disease.

In a preferred embodiment, the method is for the protection or treatment of internal or external parasitic infection. For example, the method may be for the protection or treatment of heartworm or intestinal worms. In this embodiment, the bioactive agent used in the composition includes at least one anthelmintic such as moxidectin.

The composition may be configured to provide long acting delivery of the bioactive agent for at least 50 days or more. Initial studies (see best mode section) have indicated the long acting formulation may be effective for 133 or more following an initial administration. This is a significant advantage of currently available formulations such as Cydectin®.

A use, in the manufacture of a composition as substantially described above wherein at least one bioactive agent in the composition is an anthelmintic, for a long acting prevention or treatment against a parasitic infection.

Preferably, the use is for long acting prevention or treatment against heartworm or intestinal worms.

Method of Preparation

A method of preparing a long acting composition including a bioactive agent characterized by the step of adding at least one oil and at least one cyclic amide solvent to the bioactive agent.

Preferably, the method involves the steps:

a) adding the cyclic amide solvent to a manufacturing container;
b) adding the bioactive agent to the cyclic amide solvent;
c) adding the castor oil to the mixture; and
d) adding a non-aqueous carrier up to volume.

Preferably, the cyclic amide solvent is heated to approximately 40-50° C. before step b).

Preferably, the bioactive is dissolved in the cyclic amide solvent before step c.

Preferably, an antioxidant is added before step b). The inventors found this was an important step to improve the overall effectiveness/stability of the composition. This was found to be particularly the case if the cyclic amide solvent is to be heated as preferred.

BRIEF DESCRIPTION OF DRAWINGS

Further aspects of the present invention will become apparent from the ensuing description which is given by way of example only and with reference to the accompanying drawings in which:

FIG. 1 Pilot non-slaughter study on *Haemonchus contortus* larvae counts from hatched eggs to persistency and knockdown effect (comparison between Formulation 1 and Cydectin® LA injectable);

FIG. 2 Pilot non-slaughter study on *Trichostrongylus* larvae counts from hatched eggs to persistency and knockdown effect (comparison between Formulation 1 and Cydectin® LA injectable);

FIG. 3 Pilot non-slaughter study on *Cooperia* larvae counts from hatched eggs to persistency and knockdown effect (comparison between Formulation 1 and Cydectin® LA injectable);

FIG. 4 Pilot non-slaughter study on *Oesophagostomum/Chabertia* larvae counts from hatched eggs to persistency and knockdown effect (comparison between Formulation 1 and Cydectin® LA injectable);

FIG. 5 Pilot non-slaughter study on *Ostertagia* larvae counts from hatched eggs to persistency and knockdown effect (comparison between Formulation 1 and Cydectin® LA injectable).

BEST MODES FOR CARRYING OUT THE INVENTION

Example 1

Formulation 1

| | Moxidectin Injection LA | | |
|---|---|---|---|
| Sl No | Ingredients | % w/v | Function |
| 1 | Moxidectin** | 2.1 | Active ingredient |
| 2 | BHT (Butylated hydroxytoluene) | 0.05 | Antioxidant |
| 3 | NMP (Pharmasolve) | 15 | Solvent |
| 4 | Castor oil | 7 | Solvent |
| 5 | Soyabean oil | qs | Carrier |

**5% overages added to account for any minor losses in stability or losses during manufacturing.

| Tests for Formulation 1 | Specifications |
|---|---|
| Description | A clear yellow, slightly viscous solution |
| Relative Density | 0.920-0.980 @ 20° C. |
| Active: Moxidectin | 1.96-2.20% w/v (At Manufacture) |
| | 1.80-2.30% w/v (To Expiry) |
| Sterility | By Membrane Filtration Method (BP method) |
| | No growth in fluid thioglycollate medium after 14 days (minimum) incubation at 30-35° C. |
| | No growth in soyabean casein digest medium after 14 days (minimum) incubation at 20-25° C. |

Example 2

Stability Studies

| Batch Number: T1782, Batch Size: 3.5 L Storage Conditions: 25° C./60% RH Packaging: 100 mL flexipack Gamma + Fluorinated | | | | | |
|---|---|---|---|---|---|
| | Initial | 3 Months | 6 Months | 9 Months | 18 Months |
| Description | Complies | Complies | Complies | Complies | Complies |
| Relative Density | 0.944 | 0.942 | 0.943 | 0.941 | 0.943 |
| Active: Moxidectin | 2.10 | 2.11 | 2.10 | 2.10 | 2.05 |
| Sterility | Complies | Complies | Complies | Complies | Complies |

| Batch Number: T1782 Batch Size: 3.5 L Storage Conditions: 30° C./65% RH Packaging: 100 mL flexipack Gamma + Fluorinated | | | | | |
|---|---|---|---|---|---|
| | Initial | 3 Months | 6 Months | 9 Months | 18 Months |
| Description | Complies | Complies | Complies | Complies | Complies |
| Relative Density | 0.944 | 0.942 | 0.939 | 0.941 | 0.942 |
| Active: Moxidectin | 2.10 | 2.11 | 2.11 | 2.09 | 2.02 |
| Sterility | Complies | Complies | Complies | Complies | Complies |

| Batch Number: T1782, Batch Size: 3.5 L Storage Conditions: 40° C./75% RH Packaging: 100 mL flexipack Gamma + Fluorinated | | | | |
|---|---|---|---|---|
| | Initial | 3 Months | 6 Months | 9 Months |
| Description | Complies | Complies | Complies | Complies |
| Relative Density | 0.944 | 0.942 | 0.940 | 0.940 |
| Active: Moxidectin | 2.10 | 2.08 | 2.05 | 2.03 |
| Sterility | Complies | Complies | Complies | — |

Example 3

Pilot non-slaughter study on larvae counts from hatched eggs from faecal samples to assess persistency and knockdown effect (results shown in FIGS. 1-5 wherein Formulation 1 is labeled as Moxidectin LA).

The treatments were administered using a syringe (able to measure in 0.2 mL increments) and the dose to be administered to each animal was based on its liveweight, which was determined on the day of treatment (Day 0). The dose rate for the test formulation and the reference product (Cydectin Long Acting Injection for Sheep) was 1 mL/20 kg (1 mg/kg). This dose was administered by subcutaneous injection into the side of the neck just below the ear.

Faecal samples were collected after treatment at approximately weekly intervals for 19 weeks. These samples were collected directly from the rectum and weighed a minimum of 2 g. Faecal egg counts were carried out on each sample and quantitative larval cultures were carried out on pooled samples from each treatment group at each sampling time.

The pilot study illustrated the improved persistent efficacy of Formulation 1 in all the examples tested when compared to Cydectin® long acting (LA) injection for sheep, also containing 2% w/v moxidectin.

The general trend showed that Cydectin® began to lose persistency by 100 days or less, as larvae counts began to rise. In some cases this rise was gradual (FIG. 1), yet in other cases the rise was dramatic (see FIGS. 4 and 5 for example).

However, in all cases Formulation 1 showed reduced larvae counts beyond the 100 day mark. This illustrates the improved persistency of the present invention compared to the commercially available Cydectin®.

Additionally, it is clear Formulation 1 showed overall better efficacy throughout the trial period compared to Cydectin®. In each of FIGS. 1-5, Formulation 1 remained close to the base line, whereas the Cydectin often showed deviations from the base line as shown in FIGS. 2, 3, 4 and 5).

Example 4

Pilot slaughter efficacy study to evaluate the knock-down efficacy of formulation 1, as per example 1, against a natural mixed infection of roundworms in sheep when administered at the recommended minimum dose rate, with a comparison with Cydectin® LA injectable. The study involved the determination of total worm counts when the animals were slaughtered 13 days after the administration of the treatments, along with faecal sample larval culture data at 7 and 13 days after treatment.

Efficacy based on faecal sample larval culture data 7 and 13 days after treatment is shown in the Table 1 below. Efficacy based on total adult worm count from abomasum, small intestine and large intestine assays 13 days after treatment is shown in Table 2 below.

These initial results showed no significant difference between the efficacy of Formulation 1 and the Cydectin® LA reference. This illustrates that Formulation 1 maintains an appropriate knockdown effect compared to the commercially available Cydectin® product.

TABLE 1

The number and level of control (%) of each parasite species 7 and 13 days after treatment with Moxidectin LA Injection or Cydectin Long Acting Injection based on faecal sample larval culture data and compared to the untreated controls

| | Days after treatment | | | | | |
|---|---|---|---|---|---|---|
| | 7 Product administered | | | 13 Product administered | | |
| Parasite Species | Moxidectin LA Injection | Cydectin LA | Untreated | Moxi LA Injection | Cydectin | Untreated |
| *Haemonchus* | 100% (0) | 100% (0) | 10800 | 100% (0) | 100% (0) | 5200 |
| *Ostertagia* | 95.8% (275) | 95.8% (271) | 6480 | 99.6% (14) | 98.4% (53) | 3380 |
| *Trichostrongylus* | 82.1% (155) | 63.1% (319) | 864 | 95.1% (64) | 96.8% (41) | 1300 |
| *Cooperia* | 100% (0) | 100% (0) | 2160 | 100% (0) | 100% (0) | 2340 |
| *Oesoph/Chabertia* | 100% (0) | 100% (0) | 1296 | 100% (0) | 100% (0) | 780 |

(Number in brackets indicates the actual number of larvae found)

TABLE 2

Efficacy (%) [1] of the test and reference products against $5^{th}$ stage (adult) worms 13 days after treatment, based on total worm counts in comparison to the untreated controls

| | Abomasum | | | Small intestine | | | | Large intestine | | |
|---|---|---|---|---|---|---|---|---|---|---|
| Product | *Haem* | *Ost* | *T. axei* | *Nem* | *Trich* | *Coop* | *Strong* | *Oes* | *Chab* | *Trichu* |
| Moxi LA | >99.9 | >99.9 | >99.9 | 99.9 | 90.6 | 99.9 | 87.8 | >99.9 | >99.9 | >99.9 |
| Cydectin LA | >99.9 | >99.9 | >99.9 | 99.9 | 95.7 | >99.9 | 96.6 | >99.9 | >99.9 | >99.9 |

[1] based on % reduction of geometric means in comparison to the untreated control animals
*Haem* = *Haemonchus contortus*, *Ost* = *Ostertagia circumcincta*, *Nem* = *Nematodirus* sp., *Trich* = *Trichostrongylus* sp. *Coop* = *Cooperia* spp. *Strong* = *Strongyloides*, *Oes* = *Oesophagostomum* sp. *Chab* = *Chabertia* and *Trichu* = *Trichuris* sp Aspects of the present invention have been described by way of example only and it should be appreciated that modifications and additions may be made thereto without departing from the scope thereof as defined in the appended claims.

What we claim is:

1. A long-acting veterinary pharmaceutical composition comprising a therapeutically effective amount of a bioactive agent, a non-aqueous carrier, and a solvent system comprising castor oil and at least one cyclic amide;
wherein the bioactive agent is an anthelmintic compound; and
wherein the cyclic amide is a pyrrolidone.

2. The composition as claimed in claim 1 wherein the cyclic amide is N-Methylpyrrolidone (NMP).

3. The composition as claimed in claim 1 wherein the cyclic amide is present in an amount between 1-50% w/v.

4. The composition as claimed in claim 1 wherein the castor oil is present in an amount between 1-20% w/v.

5. The composition as claimed in claim 1 wherein the composition is an injectable composition.

6. The composition as claimed in claim 1 wherein the anthelmintic is selected from the group consisting of avermectin, moxidectin, milbemycin, ivermectin, abamectin, doramectin, eprinomectin and selamectin.

7. The composition as claimed in claim 1 wherein the anthelmintic compound is present in an amount between 0.005 to 5% w/v.

8. The composition as claimed in claim 6 wherein the anthelmintic compound is moxidectin.

9. The composition as claimed in claim 1 wherein the non-aqueous carrier comprises an oil selected from the group consisting of canola oil, corn oil, cottonseed oil, olive oil, peanut oil, sesame oil, soybean oil, safflower oil, coconut oil, sunflower oil, palm oil, monoglyceride, diglyceride and triglyceride medium chain succinic acid triglyceride.

10. The composition as claimed in claim 1 wherein the cyclic amide is present in an amount of approximately 15% w/v.

11. The composition as claimed in claim 1 wherein the castor oil is present in an amount of approximately 7% w/v.

12. The composition as claimed in claim 1 further comprising an antioxidant.

13. The composition as claimed in claim 12 wherein the antioxidant is butylated hydroxytoluene (BHT).

14. The composition as claimed in claim 12 wherein the antioxidant is present in an amount between 0.001 to 10% w/v.

15. The composition as claimed in claim 12 wherein the antioxidant is present in an amount of approximately 0.05% w/v.

16. A method of treating a parasitic infection in an animal in need thereof comprising administering to the animal a composition as claimed in claim 1.

17. The method as claimed in claim 16 wherein the treatment of the parasitic infection persists for at least 50 days after administration of the composition.

18. A method of preparing a long-acting veterinary pharmaceutical composition according to claim 1 comprising:
  a) adding the bioactive agent to the cyclic amide solvent;
  b) adding castor oil to the bioactive agent/cyclic amide mixture; and
  c) adding a non-aqueous carrier to the resulting mixture.

* * * * *